US006281375B1

(12) United States Patent
Kodali et al.

(10) Patent No.: US 6,281,375 B1
(45) Date of Patent: *Aug. 28, 2001

(54) BIODEGRADABLE HIGH OXIDATIVE STABILITY OILS

(75) Inventors: Dharma R. Kodali, Plymouth, MN (US); Zhegong Fan; Lorin R. DeBonte, both of Fort Collins, CO (US)

(73) Assignee: Cargill, Incorporated, Wayzata, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,743

(22) Filed: Aug. 3, 1998

(51) Int. Cl.$^7$ .................................................. C07C 57/00

(52) U.S. Cl. .............................................. 554/227; 554/2

(58) Field of Search ............................................ 559/227

(56) References Cited

U.S. PATENT DOCUMENTS

| | | | |
|---|---|---|---|
| 4,783,274 | 11/1988 | Jokinen et al. | 252/32.7 |
| 4,925,581 | 5/1990 | Erickson et al. | 252/48.2 |
| 4,970,010 | 11/1990 | Erickson et al. | 252/48.6 |
| 4,987,071 | 1/1991 | Cech et al. | 435/91 |
| 5,188,958 | 2/1993 | Moloney et al. | 435/240.4 |
| 5,204,253 | 4/1993 | Sanford et al. | 435/172.3 |
| 5,254,678 | 10/1993 | Haseloff et al. | 536/23.2 |
| 5,413,725 | 5/1995 | Lal et al. | 252/18 |
| 5,451,334 | 9/1995 | Bongardt et al. | 252/56 R |
| 5,530,186 | 6/1996 | Hitz et al. | 800/205 |
| 5,633,151 | 5/1997 | McNeil | 435/134 |
| 5,703,022 | 12/1997 | Floyd | 508/345 |
| 5,773,391 | 6/1998 | Lawate et al. | 508/257 |

FOREIGN PATENT DOCUMENTS

| | | |
|---|---|---|
| WO 93/11245 | 6/1993 | (WO) . |
| WO 94/11516 | 5/1994 | (WO) . |
| WO 95/13390 | 5/1995 | (WO) . |
| WO 95/15387 | 6/1995 | (WO) . |
| WO 96/06936 | 3/1996 | (WO) . |
| WO 96/24674 | 8/1996 | (WO) . |
| WO 97/21340 | 6/1997 | (WO) . |

OTHER PUBLICATIONS

Taylor et al., "Triacylglycerol Bioassembly in Microspore–Derived Embryos of Brassica napus L. cv Reston", *Plant Physiol.*, 1991, 97:65–79.

Ray et al., "The primary defect in developing seed from the high oleate variety of peanut (Arachis hypogaea L.) is the absence of $\Delta^{12}$–desaturase activity", *Plant Science*, 1993, 91:15–21.

Trani et al., "Enzymatic Synthesis of Trierucin from High–Erucic Acid Rapeseed Oil", *JAOCS*, 70(10):961–964.

Lassner et al., "Lysophosphatidic Acid Acyltransferase from Meadowfoam Mediates Insertion of Erucic Acid at the sn–2 Position of Triacylglycerol in Transgenic Rapeseed Oil", *Plant Physiol.*, 1995, 109:1389–1394.

Jalani et al., "Improvement of Palm Oil Through Breeding and Biotechnology", *JAOCS*, 1997, 74(11):1451–1455.

Zou et al., "Modification of Seed Oil Content and Acyl Composition in the Brassicaceae by Expression of a Yeast sn–2 Acyltransferase Gene", *Plant Cell*, 1997, 9:909–923.

Okuley et al., "Arabidopsis FAD2 Gene Encodes the Enzyme That is Essential for Polyunsaturated Lipid Synthesis," *Plant Cell*, 1994, 6:147–158.

Perriman et al., "Effective ribozyme delivery in plant cells," *Proc. Natl. Acad. Sci. USA*, 1995, 92:6175–6179.

de Feyter et al., "Expressing Ribozymes in Plants," *Methods Mol. Biol.*, Edited by P.C. Turner, Humana Press Inc., Tolowa, NJ, 74:403–415, 1992.

Arondel et al., "Map–Based Cloning of a Gene Controlling Omega–3 Fatty Acid Desaturation in Arabidopsis," *Science*, 1992, 258:1353–1355.

Yadav et al., "Cloning of Higher Plant ω–3 Fatty Acid Desaturases," *Plant Physiol*, 1993, 103:467–476.

Thompson et al., "Primary structures of the precursor and mature forms of stearoyl–acyl carrier protein desaturase from safflower embryos and requirement of ferredoxin for enzyme activity," *Proc. Natl. Acad. Sci. USA*, 1991, 88:2578–2582.

Shanklin et al., "Stearyol–acyl–carrier–protein desaturase from higher plants is structurally unrelated to the animal and fungal homologs," *Proc. Natl. Acad. Sci USA*, 1991, 88:2510–2514.

Stukey et al., "The OLE1 Gene of Saccharomyces cerevisiae Encodes the $\Delta 9$ Fatty Acid Desaturase and Can Be Functionally Replaced by the Rat Stearoyl–CoA Desatuase Gene", *J. Biol. Chem.*, 1990, 265(33):20144–20149.

Thiede et al., "Construction and Sequence of cDNA for Rat Liver Stearyl Coenzyme A Desaturase", *J. Biol. Chem.*, 1986, 261(28):13230–13235.

Kaestner et al., "Differentiation–induced Gene Expression in 3T3–L1 Preadipocytes", *J. Biol. Chem.*, 1989, 264(25):14755–14761.

Murphy et al., "Biosynthesis of Seed Storage Products during Embryogenesis in Rapeseed, Brassica napus", *J. Plant Physiol.*, 1989, 135:63–69.

van der Krol et al., "Modulation of Eukaryotic Gene Expression by Complementary RNA or DNA Sequences", *BioTechniques*, 1988, 6(10):958–976.

Sheehy et al., "Reduction of polygalacturonase activity in tomato fruit by antisense RNA", *Proc. Natl. Acad. Sci. USA*, 1988, 85:8805–8809.

(List continued on next page.)

*Primary Examiner*—Deborah D. Carr
(74) *Attorney, Agent, or Firm*—Fish & Richardson P.C.

(57) ABSTRACT

A triacylglycerol containing oil having a 1,3-dierucoyl 2-oleoyl glycerol (EOE) content of at least 50% is described. Plants for producing an oil having a high EOE content are also described.

10 Claims, No Drawings

OTHER PUBLICATIONS

Cannon et al., "Organ–specific modulation of gene expression in transgenic plants using antisene RNA", *Plant Mol. Biol.*, 1990, 15:39–47.

Ch'ng et al., "Antisense RNA complementary to 3' coding and noncoding sequences of creatine kinase is a potent inhibitor of translation in vivo", *Proc. Natl. Acad. Sci. USA*, 1989, 86:10006–10010.

Napoli et al., "Introduction of a Chimeric Chalcone Synthase Gene into Petunia Results in Reversible Co–Suppression of Homologous Genes in trans", *Plant Cell,* 1990, 2:279–289.

van der Krol et al., "Flavonoid Genes in Petunia: Addition of a Limited Number of Gene Copies May Lead to a Suppression of Gene Expression", *Plant Cell,* 1990, 2:291–299.

Smith et al., "Expression of a truncated tomato polygalacturonase gene inhibits expression of the endogenous gene in transgenic plants", *Mol Gen. Genet.,* 1990, 224:477–481.

McVetty et al., "Venus high erucic acid, low glucosinolate summer rape", *Can. J. Plant Sci.,* 1996, 76(2):341–342.

Scarth et al., "Mercury high erucic low glucosinolate summer rape", *Can. J. Plant Sci.,* 1995, 75(1):205–206.

McVetty et al., "Neptune high erucic acid, low glucosinolate summer rape", *Can. J. Plant Sci.,* 1996, 76(2):343–344.

Cvitkovic, "A Thin–Film Test for Measurement of the Oxidation and Evaporation of Ester–Type Lubricants", *ASLE Trans,* 1979, 22(4)395–401.

Walkerpeach et al., "Agrobacterium–mediated gene transfer to plant cells: cointegrate and binary vector systems", *Plant Mol. Biol. Manual,* 1994, B1:1–19, Kluwer Academic Publishers.

Topfer et al., "Modification of Plant Lipid Synthesis", *Science,* May 5, 1995, 268:681–685.

Arondel et al., *Science*, 1992, 258;1353–1355.

Cannon et al., *Plant Molecular Biology*, 1990, 15;39–47.

Ch'ng, et al., *Proc. Natl. Acad. Sci. USA*, 1989, 86;10006–10010.

Cvitkovic, *ASLE Transactions*, 1978, 22(4):395–401.

de Feyter et al., *Methods in Molecular Biology*, 74:403–415, 1992.

Jalani et al., *JAOCS*, 1997, 74(11):1451–1455.

Kaestner et al., *J. Biol. Chem.*, 1989, 264(25):14755–14761.

Lassner et al., *Plant Physiol.*, 1995, 10–:1389–1394.

McVetty et al., *Can. J. Plant. Sci.*, 1996, 76(2)343–344.

McVetty et al., *Can. J. Plant. Sci.*, 1996, 76(2):341–342.

Ch'ng, et al. *Proc. Natl. Acad. Sci. USA*, 1989, 86:10006–10010.

Cvitkovic, *ASLE Transactions*, 1978,22(4):395–401.

de Feyter et al.,*Methods in Molecular Biology*, 74:403–415, 1992.

Jalani et al., *JAOCS*, 1997, 74(11):1451–1455.

Kaestner et al.,*J. Biol. Chem.*, 1989, 264(25):14755–14761.

Lassner et al., *Plant Physiol.*, 1995, 109:1389–1394.

McVetty et al., *Can. J. Plant Sci.*, 1996, 76(2):343–344.

McVetty et al., *Can. J. Plant Sci.*, 1996, 76(2):341–342.

Murphy et al., *J. Plant Physiol.*, 1989, 135:63–69.

Napoli et al., *The Plant Cell*, 1990, 2:279–289.

Okuley et al., *The Plant Cell*, 1994, 6(1):147–158.

Perriman et al., *Proc. Natl. Acad. Sci. USA*, 1995,92:6175–6179.

Ray et al., *Plant Science*, 1993,91:15–21.

Scarth et al., *Can. J. Plant Sci.*, 1995,75(1):205–206.

Shanklin et al., *Proc. Natl. Acad. Sci. USA*, 1991,88:2510–2514.

Sheehy et al., *Proc. Natl. Acad. Sci. USA*, 1988, 85:8805–8809.

Smith et al., *Mol Gen Genet*, 1990, 224:477–481.

Stukey et al., *J. Biol. Chem.*, 1990, 265(33):20144–20149.

Taylor et al., *Plant Physiol.*, 1991,97:65–79.

Thiede et al., *J. Biol. Chem.*, 1986, 261(28):13230–13235.

Thompson et al., *Proc. Natl. Acad. Sci. USA*, 1991, 88:2578–2582.

Topfer et al., *Science*, 1995, 268:681–686.

Trani et al., *JAOCS*, 1993, 70(10):961–964.

van der Krol et al., *The Plant Cell*, 1990, 2:291–299.

van der Krol et al., *BioTechniques*, 1988, 6(10):958–976.

Walkerpeach et al., *Plant Mol. Biol.*, 1994, B1:1–19.

Yadav et al., *Plant Physiol.*, 1993, 103:467–476.

Zou et al., *The Plant Cell*, 1997, 9:909–923.

BIODEGRADABLE HIGH OXIDATIVE STABILITY OILS

BACKGROUND OF THE INVENTION

This invention relates to oils having a 1,3-dierucoyl 2-oleoyl glycerol (EOE) content of at least about 50%, based on total triacylglycerol composition, and use of such oils in industrial applications.

Oils used in industrial applications are typically petroleum based hydrocarbons that can damage the environment as well as pose health risks to people using them. Plant oils are an environmentally friendly alternative to petroleum based products and are based on a renewable natural resource. The major components of plant oils are triacylglycerols, which are three fatty acid chains esterified to a glycerol molecule. The polar glycerol regions and non-polar hydrocarbon regions align at the boundaries of the metal surfaces, and thus have better lubricant properties than petroleum hydrocarbons.

Two main properties of plant oils hinder their use for industrial applications. Most plant oils do not possess both of these characteristics. First, the oils must be liquid and have a reasonable viscosity at low temperatures. For example, high erucic purified rapeseed oil has a pour point of −16° C., but undergoes a significant increase in viscosity with decreasing temperatures.

Second, the oils must have high oxidative stability. In general, oxidative stability is related to the degree of unsaturation present in the fatty acids. Reaction with oxygen can lead to polymerization and cross-linking of the fatty acids and an increased viscosity. Saturated hydrocarbon based oils have no unsaturation and therefore have high oxidative stability.

SUMMARY OF THE INVENTION

The invention is based on oils having a high EOE content and uses for such oils in industrial applications. The oils can be synthetic or can be produced by plants.

In one aspect, the invention features a triacylglycerol containing oil having a 1,3-dierucoyl 2-oleoyl glycerol content of at least about 50% based on total triacylglycerol composition. In particular embodiments, the oil has a 1,3-dierucoyl 2-oleoyl glycerol content of from about 60% to about 90% or from about 75% to about 90%. Oils of the invention have an oxidative stability of from about 80 AOM hours to about 300 AOM hours in the absence of added antioxidants. In particular, the oxidative stability is from about 84 AOM hours to about 120 AOM hours in the absence of added antioxidants. The viscosity index of such oils is greater than about 195.

In another aspect, the invention features a plant having a seed-specific reduction in delta-12 desaturase activity in comparison with a corresponding wild-type plant. Suitable plants are from species that naturally produce erucic acid. Such modified plants produce seeds yielding an oil comprising from about 50% to about 70% erucic acid and from about 25% to about 35% oleic acid. In certain embodiments, the plants further have a seed-specific reduction in palmitoyl ACP thioesterase activity and a seed-specific increase in delta-9 desaturase activity in comparison with corresponding wild-type plants. The plants also can have a seed-specific reduction in delta-15 desaturase activity in comparison with corresponding wild-type plants.

The invention also features a transgenic plant of a species that naturally produces erucic acid, wherein the transgenic plant has at least one nucleic acid construct. The nucleic acid construct includes a regulatory sequence operably linked to afad2 coding sequence. The transgenic plant exhibits a seed-specific reduction in delta-12 desaturase activity in comparison with a corresponding non-transgenic plant, and produces seeds yielding an oil comprising from about 50% to about 70% erucic acid and from about 25% to about 35% oleic acid, based on total fatty acid composition. Progeny of such transgenic plants produce seeds yielding an oil having the erucic acid content and the oleic acid content of the parent.

Transgenic plants of the invention further can have at least one construct having a regulatory sequence operably linked to a palnitoyl ACP thioesterase coding sequence and a regulatory sequence operably linked to a delta-9 desaturase coding sequence. Such plants exhibit a seed-specific increase in delta-9 desaturase activity and a seed-specific reduction in palmitoyl ACP thioesterase activity in comparison with corresponding non-transgenic plants. In some embodiments, the transgenic plant also contains at least one construct having a regulatory sequence operably linked to a fad3 coding sequence, and exhibits a seed-specific reduction in delta-15 desaturase activity in comparison with a corresponding non-transgenic plant.

The invention also features a method of producing an endogenous vegetable oil. The method includes crushing seeds of plants of the invention, and extracting oil therefrom.

In another aspect, an endogenous oil having an erucic acid content of from about 50% to about 70% and an oleic acid content of from about 25% to about 35%, based on total fatty acid composition is described. Triacylglycerols of such oils contain about 75% or greater 1,3-dierucoyl 2-oleoyl glycerol. In particular embodiments, the triacylglycerols of the oil contain about 75% to about 90% 1,3-dierucoyl 2-oleoyl glycerol.

The invention also features a high oxidative stability composition including a vegetable oil and an amount of 1,3-dierucoyl 2-oleoyl glycerol effective to increase oxidative stability of the vegetable oil.

The invention also features a hydraulic oil composition including an oil having a 1,3-dierucoyl 2-oleoyl glycerol content of at least 50% based on total triacylglycerol composition and an additive. The additive can be, for example, an antioxidant, anti-rust additive, anti-wear additive, pour point depressant, viscosity-index improver, anti-foam additive or a combination thereof and is present in an amount from about 0.01% to about 20% based on the weight of the composition.

A lubrication additive including a triacylglycerol containing oil having a 1.3 dierucoyl 2-oleoyl glycerol content of at least about 50% based on total triacylglycerol composition is also described. The additive is effective for reducing friction when present in lubrication fluid in amounts from about 2% to about 20% by weight in the lubrication fluid.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Oils having a specific triacylglycerol composition are featured in the invention. In particular, triacylglycerol containing oils having an erucic acid moiety at the sn-1 and sn-3 positions and an oleic acid moiety at the sn-2 position of glycerol (1,3-dierucoyl 2-oleoyl glycerol, EOE) are featured.

In one aspect, the invention features a triacylglycerol containing oil including an EOE content of about 50% or greater based on the total triacylglycerol (TAG) composition of the oil. As used herein, a "triacylglycerol containing oil" refers to synthetic or natural oils composed primarily of triacylglycerols. In particular embodiments, the triacylglycerol containing oil can include an EOE content of about 60% to about 90% and is preferably from about 75% to about 90%. The proportions of TAGs in an oil of the invention that are EOE can be readily determined according to AOCS Official Method Ce 5B-89. Individual TAGs are identified by comparison with external or internal standards and can be quantified using a non-linear quadratic fit curve. The oils of the invention can be synthetic or can be from a natural source.

Synthesis of EOE

A triacylglycerol containing oil having an EOE content of at least 50% based on total triacylglycerol composition can be chemically synthesized using 1,3 dihydroxyacetone and free erucic and oleic fatty acids as starting materials. Oils chemically synthesized as described herein have EOE contents of 80% or greater, and preferably greater than 90%. In the first step, 1,3 dihydroxyacetone dimer and erucic acid can be reacted in the presence of dicyclohexylcarbodiimide and 4-dimethylaminopyridine to form 1,3 dierucoylpropanone. The ketone group of 1,3 dierucoylpropanone can be reduced using, for example, sodium borohydride and water to form 1,3 dierucoylpropanol. EOE can be produced by reacting 1,3 dierucoylpropanol and oleic acid in the presence of dicyclohexylcarbodiimide and 4-dimethylaminopyridine to form 1,3 dierucoyl 2-oleoyl propane.

Alternatively, high erucic acid rapeseed (HEAR) oil can be hydrolyzed by a lipase from *Candida rugosa* (Sigma Chemical Company, St. Louis, Mo.) to obtain 1,3 dierucin and free fatty acids. In this procedure, an aqueous solution of *C. rugosa* lipase can be added to the HEAR oil and maintained at room temperature for about 18 hours with constant stirring. The hydrolyzed oil can be extracted with an equal ratio of chloroform and water. The chloroform layer can be recovered, dried over magnesium sulfate, filtered and evaporated to obtain an oily residue. After washing with cold ethanol, the resulting solid can be filtered to remove free-fatty acids, and washed again with cold ethanol to yield 1,3 dierucin. Dierucin can be purified by HPLC using a CSC-Spherisorb-ODS3 column and a equal ratio of acetone and acetonitrile as the mobile phase. See, Trani, M., 1993, *J. Am. Oil Chem. Soc.*, 70(10):961–964. As another alternative, dierucin can be obtained from Sigma Chemical Company (St. Louis, Mo.). An oil having an EOE content of at least about 50% can be produced from purified 1,3 dierucin by reacting it with free oleic acid in the presence of an immobilized non-specific lipase, such as SP382 (Novo).

Preparation of EOE From Natural Sources

EOE can also be purified from endogenous oils such as that extracted from high erucic acid rapeseed or from seeds of various Crambe species. Triacylglycerols extracted from conventional HEAR oil predominantly contain oleic (18:1), linoleic (18:2) or linolenic (18:3) at the sn-2 position, with erucic (22:1) composing less than 0.5 mol % of the fatty acid at the sn-2 position. Oils from HEAR-type rapeseed and Crambe contain approximately 17% and 46% EOE, respectively. TAGs from *C. abyssinica* or *C. hispanica* can be separated using HPLC according to AOCS Official Method Ce 5B-89. EOE purified in this manner has a retention time of about 17 minutes. Alternatively, EOE can be HPLC purified using a ChromSphere Lipids column (Chrompack, Raritan, N.J.). A sequential combination of solvents including, hexane:toluene, toluene:ethyl acetate, and toluene:99% formic acid, can be used to elute the TAGs. Lassner, M. W. et al., 1995, *Plant Physiol.*, 109:1389–1394. When EOE is purified by the methodology of Lassner et al., it has a retention time of about 13 minutes.

Plants that naturally produce erucic acid can be manipulated to produce high levels of EOE through genetic-engineering, mutagenesis or combinations thereof. Endogenous oils having an erucic acid content of from about 50% to about 70% and an oleic acid content of from about 25% to about 35%, based on total fatty acid composition can be obtained from crushing seeds of such plants and extracting the oil therefrom. The EOE content of such oils is preferably from about 75% to about 90% of the total triacylglycerol composition.

Plants that naturally produce erucic acid and are suitable for such manipulation include Brassica species such as *B. napus, B. juncea* and *B. rapa*, Crambe species such as *C. abyssinica* and *C. hispanica*, and Limnanthes species such as *L. alba alba* and *L. douglasii* (meadowfoam). In general, the levels of saturated and polyunsaturated fatty acids are decreased in the modified plants in order to increase the oleic acid and erucic acid content and consequently, to increase the EOE content.

Transgenic plants can be obtained by introducing at least one nucleic acid construct into a plant cell as described herein. Seeds produced by a transgenic plant can be grown and selfed (or outcrossed and selfed) to obtain plants homozygous for the construct. Seeds can be analyzed to identify those homozygotes having the desired expression of the construct. Transgenic plants can be entered into a breeding program, e.g., to increase seed, to introgress the novel construct into other lines or species, or for further selection of other desirable traits. Alternatively, transgenic plants can be obtained by vegetative propagation of a transformed plant cell, for those species amenable to such techniques.

As used herein, a transgenic plant also refers to progeny of an initial transgenic plant. Progeny includes descendants of a particular plant or plant line, e.g., seeds developed on an instant plant. Progeny of an instant plant also includes seeds formed on $F_1$, $F_2$, $F_3$, and subsequent generation plants, or seeds formed on $BC_1$, $BC_2$, $BC_3$, and subsequent generation plants.

Transgenic techniques for use in the invention include, without limitation, Agrobacterium-mediated transformation, electroporation and particle gun transformation. Illustrative examples of transformation techniques are described in U.S. Pat. No. 5,204,253 (particle gun) and U.S. Pat. No. 5,188,958 (Agrobacterium). Transformation methods utilizing the Ti and Ri plasmids of Agrobacterium spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art.

Transgenic Brassica or Crambe plants can be created that exhibit a seed-specific reduction in delta-12 fatty acid desaturase activity in comparison with a corresponding non-transgenic plant. Such plants have elevated levels of EOE in their seed oil. Seeds from such plants can yield an oil including from about 50% to about 70% erucic acid and from about 25% to about 35% oleic acid based on total fatty acid composition. Oil composition is typically analyzed by crushing and extracting fatty acids from bulk seed samples (e.g., 10 seeds). Fatty acid triglycerides in the seed are hydrolyzed and converted to fatty acid methyl esters. Those seeds having an altered fatty acid composition may be identified by techniques known to the skilled artisan, e.g., gas-liquid chromatography (GLC) analysis of a bulked seed sample, a single seed or a single half-seed. Half-seed analysis is well known in the art to be useful because the viability of the embryo is maintained and thus those seeds having a desired fatty acid profile may be planted to form the next generation. However, bulk seed analysis typically yields a more accurate representation of the fatty acid profile of a given genotype. Fatty acid composition can also be determined on larger samples, e.g., oil obtained by pilot plant or commercial scale refining, bleaching and deodorizing of endogenous oil in the seeds.

The enzyme delta-12 fatty acid desaturase (also known as oleic desaturase) is involved in the enzymatic conversion of oleic acid to linoleic acid. A microsomal delta-12 desaturase has been cloned and characterized using T-DNA tagging. Okuley, et al., Plant Cell 6:147–158 (1994). The nucleotide sequences of higher plant genes encoding microsomal delta-12 fatty acid desaturase are described in Lightner et al., WO94/11516. The gene encoding delta-12 fatty acid desaturase is referred to as fad2 in Brassica and Arabidopsis.

A seed-specific reduction in delta-12 desaturase activity can be achieved by techniques including, but not limited to, antisense, ribozyme cleavage, dominant negative suppression and co-suppression. These phenomena can significantly reduce expression of the gene product of the native gene. A reduction in fad2 gene expression and delta-12 desaturase activity can be inferred from the decreased level of reaction product (e.g., decreased 18:2) and the increased level of substrate in seeds compared with the corresponding levels in non-transgenic plants.

Transgenic plants of the invention can also exhibit a seed-specific reduction in palmitoyl ACP thioesterase activity and a seed-specific increase in delta-9 desaturase activity in comparison with a corresponding non-transgenic plant. Palmitoyl-ACP thioesterase or thioesterase-2 hydrolyzes palmitoyl-ACP into free palmitate and ACP. A seed-specific reduction in palmitoyl-ACP thioesterase activity prevents the release of palmitate from the ACP carrier protein and results in elongation of palmitoyl-ACP to stearoyl-ACP. Plant palmitoyl-ACP thioesterase sequences are described in WO 95/13390, WO 96/06436 and U.S. Pat. No. 5,530,186. A seed-specific reduction in palmitoyl-ACP thioesterase activity can be achieved by techniques including, but not limited to, mutagenesis, antisense, ribozyme cleavage, dominant negative suppression and co-suppression.

Delta-9 desaturase catalyzes the desaturation of stearoyl-ACP (18:0) at the Δ9 position, to yield oleoyl-ACP (18:1) and is often referred to as a "stearoyl-ACP desaturase" because of its high activity toward stearate. Nucleotide sequences encoding microsomal delta-9 desaturases from yeast, rat, and mice have been described. Stukey, et al., J. Biol. Chem., 265:20144–20149, (1990); Thiede et al., J. Biol. Chem., 261:13230–13235, (1986); Kaestner et al., J. Biol. Chem., 264:14755–14761, (1989). Nucleotide sequences encoding soluble delta-9 desaturases from higher plants have also been described. Thompson et al., Proc. Natl. Acad. Sci. USA, 88:2578–2582, (1991); Shanklin et al., Proc. Natl. Acad. Sci. USA, 88:2510–2514. Delta-9 desaturase can be overexpressed by operably linking a delta-9 desaturase coding sequence to a seed-specific regulatory element in sense orientation and introducing the construct into a plant cell using techniques discussed above.

Transgenic plants of the invention can also exhibit a seed-specific reduction in delta-15 fatty acid desaturase activity in comparison with a corresponding non-transgenic plant. Delta-15 fatty acid desaturase (also known as linoleic acid desaturase) is involved in the enzymatic conversion of linoleic acid to α-linolenic acid. The gene encoding delta-15 fatty acid desaturase is referred to as fad3 in Brassica and Arabidopsis. Sequences of higher plant genes encoding microsomal and plastid fad3 desaturases are disclosed in Yadav, N., et al., Plant Physiol., 103:467–476 (1993), WO 93/11245 and Arondel, V. et al., Science, 258:1353–1355 (1992). A seed-specific reduction in delta-15 desaturase activity can be achieved by techniques including, but not limited to, antisense, ribozyme cleavage, dominant negative suppression and co-suppression, as described above. Progeny of such plants produce seeds yielding an oil having from about 50% to about 70% erucic acid and from about 25% to about 35% oleic acid.

The preparation of antisense and co-suppression constructs for inhibition of desaturase or thioesterase activity may utilize fragments containing the transcribed sequence of the desaturase or thioesterase gene. Suitable nucleic acid constructs include a regulatory sequence operably linked to a fad2 coding sequence for reduction in delta-12 desaturase activity. A suitable nucleic acid construct for reduction of delta-15 desaturase activity includes a regulatory sequence operably linked to a fad3 coding sequence. Regulatory sequences typically do not themselves code for a gene product. Instead, regulatory sequences affect the expression level of the coding sequence. Examples of regulatory sequences are known in the art and include, without limitation, promoters of genes expressed during embryogenesis, e.g., a napin promoter, a phaseolin promoter, an oleosin promoter, a cruciferin promoter and constitutive promoters such as the cauliflower mosaic virus 35S promoter. Native regulatory sequences, including the native promoters, of delta-9, delta-12 and delta-15 fatty acid desaturase genes and palmitoyl-ACP thioesterase also can be used in constructs of the invention. Other examples of suitable regulatory sequences include enhancers or enhancer-like elements, introns and 3' non-coding regions such as poly A sequences. Further examples of suitable regulatory sequences for the proper expression of delta-9, delta-12 or delta-15 desaturase and palmitoyl-ACP thioesterase coding sequences are known in the art.

In preferred embodiments, regulatory sequences are seed-specific, i.e., the particular gene product is preferentially expressed in developing seeds and expressed at low levels or not at all in the remaining tissues of the plant. Seed-specific regulatory sequences preferably stimulate or induce expression of the recombinant desaturase coding sequence fragment at a time that coincides with or slightly precedes expression of the native desaturase gene. Murphy et al., J. Plant Physiol., 135:63–69 (1989).

Antisense RNA has been used to inhibit plant target genes in a tissue-specific manner. van der Krol et al., Biotechniques, 6:958–976 (1988). Antisense inhibition has been shown using the entire cDNA sequence as well as a partial cDNA sequence. Sheehy et al., Proc. Natl. Acad. Sci.

USA. 85:8805–8809 (1988); Cannon et al., *Plant Mol. Biol.*, 15:39–47 (1990). There is also evidence that 3' non-coding sequence fragment and 5' coding sequence fragments can play important roles in antisense inhibition. Ch'ng et al., *Proc. Natl. Acad. Sci. USA,* 86:10006–10010 (1989); Cannon et al., supra. Antisense nucleic acid constructs include a partial or a full-length coding sequence operably linked to at least one suitable regulatory sequence in antisense orientation.

Desirable alterations in fatty acid levels in the seed oil of plants can be produced using a ribozyme. Ribozyme molecules designed to cleave delta-12 or delta-15 desaturase, or palmitoyl-ACP thioesterase mRNA transcripts can be used to prevent expression of delta-12 or delta-15 desaturases and palmitoyl-ACP thioesterase. While various ribozymes that cleave mRNA at site-specific recognition sequences can be used to destroy desaturase mRNAs, hammerhead ribozymes are particularly useful. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is well known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., *Proc. Natl. Acad. Sci. USA,* 92(13):6175–6179 (1995); de Feyter, R. and Gaudron, J., *Methods in Molecular Biology,* Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators are also useful. See, for example, U.S. Pat. No. 4,987,071.

The phenomenon of co-suppression has also been used to inhibit plant target genes in a tissue-specific manner. Co-suppression of an endogenous gene using a full-length cDNA sequence as well as a partial cDNA sequence are known. Napoli et al., *The Plant Cell,* 2:279–289 (1990); van der Krol et al., *The Plant Cell,* 2:291–299 (1990); Smith et al., *Mol. Gen. Genetics,* 224:477–481 (1990). Co-suppression of delta-12 or delta-15 desaturase activity in plants can be achieved by expressing, in the sense orientation, the entire or partial coding sequence of a fad2 or fad3 gene. See, for example, WO 94/11516.

Mutagenesis can also be used to reduce delta-12 desaturase, delta-15 desaturase or palmitoyl thioesterase activity in plants. Mutagenic agents can be used to induce random genetic mutations within a population of seeds or regenerable plant tissue. Suitable mutagenic agents include, for example, ethyl methane sulfonate, methyl N-nitrosoguanidine, ethidium bromide, diepoxybutane, x-rays, UV rays and other mutagens known in the art. The treated population, or a subsequent generation of that population, is screened for reduced desaturase or thioesterase activity that results from the mutation. Mutations can be in any portion of a gene, including coding sequence, intron sequence and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product.

Examples of mutant delta-12 desaturase genes are found in WO97/21340. Plants exhibiting either reduced desaturase or reduced thioesterase activity can be used to create plant lines that produce seeds having an EOE content of at least about 50% through conventional breeding techniques. As described above, oleic acid and erucic acid content can be increased through genetic-engineering, mutagenesis or a combination thereof. For example, the high oleic Q4275 canola plant line having a mutation in the fad2-d and fad2-f genes can be crossed with a plant line having high oleic and low linolenic characteristics. Selected plants resulting from this cross can then be crossed to high erucic acid containing lines. Suitable high erucic acid lines include, for example, Hero (HE101, HEC01), Mercury, Venus, Neptune or S89-3673 and have about 45% or more erucic acid. McVetty, P. B. E. et al., *Can. J. Plant Sci.,* 76(2):341–342 (1996); Scarth, R. et al., *Can. J. Plant Sci.* 75(1):205–206 (1995); and McVetty, P. B. E. et al., *Can J. Plant Sci.,* 76(2):343–344 (1996). Suitable high oleic and low linolenic lines include, for example, the transgenic lines 048X058 and 663-40. Line 048X058 is a result of a co-suppression event using a transgene that includes a napin promoter linked to a linoleic desaturase gene. Line 663-40 contains the 048X058 transgene as well as a second co-suppression event resulting from the introduction of a transgene that includes an oleosin promoter linked to an oleic desaturase gene.

Characterization of Oils Having an EOE Content of at Least 50%

Oils having an EOE content of at least about 50% have high oxidative stability and excellent low temperature properties. Without being bound by a particular mechanism, the high monounsaturated content and varied chain length of the fatty acids in the majority of triacylglycerols is thought to impede orderly packing of the triacylglycerols. The end methyl groups have a mismatch in molecular volume, reducing Van der Waals interaction. The different positions of the single double bond of erucic acid and oleic acid (between carbons 11–12 and between carbons 9–10, respectively) also disrupts packing and is thought to reduce $\pi$—$\pi$ electronic interactions between the adjacent chains.

The oxidative stabilities of oils having an EOE content of at least 50% are higher than other vegetable oils. Oxidative stability is related to the degree of unsaturation in the oil and can be measured, e.g., with an Oxidative Stability Index instrument, Omnion, Inc., Rockland, Mass. according to AOCS Official Method Cd 12b-92 (revised 1993). Oxidative stability is often expressed in terms of "AOM" hours. For example, oxidative stability of oils having an EOE content of at least about 50% can be from 60 AOM hours to about 120 AOM hours in the absence of added antioxidants or from about 80 AOM hours to about 120 AOM hours. In particular embodiments, the oil has an oxidative stability of about 84 AOM hours in the absence of added antioxidants. In comparison, HEAR and soy oil have oxidative stabilities of about 10 and 16 AOM hours, respectively, in the absence of added antioxidants. Synthetic EOE does not contain any natural tocopherols or other antioxidants found in plant material. EOE produced by plants may have even higher oxidative stability depending on the percentage of EOE in the plant oil.

In the presence of antioxidants, the oxidative stability of oils having an EOE content of at least 50% is from about 250 to about 600 AOM hours. Preferably, the oxidative stability is from about 380 AOM hours to about 570 AOM hours. Antioxidants such as zinc dithiophosphates, methyl dithiocarbamates, hindered phenols, phenol sulfides, metal phenol sulfides, metal salicylates, aromatic amines, phospho-sulfurized fats and olefins, sulfurized olefins, sulfurized fats and fat derivatives, sulfurized paraffins, sulfurized carboxylic acids, disalieylal-1,2,-propane diamine, 2,4-bis(alkyldithio-1,3,4-thiadiazoles) and dilauryl selenide are suitable for use. Antioxidants are typically present in amounts from about 0.001% to about 5%, based on the weight of the composition. In particular embodiments, antioxidants such as tert-butylhydroquinone (TBHQ) and Lubrizol product number OS-121056F are added and are present in amounts from about 0.001% to about 3%.

Oils having an EOE content of at least 50% based on total TAG composition have excellent low temperature viscosity properties. At −5° C., the viscosity is approximately 400 centistokes (cST) and is comparable with trimethylpropane trioleate (TMPTO). In contrast, petroleum based oils sold under the tradenames 66H and 71S (Lubrizol, Wickliffe, Ohio) have viscosities between 750 and 1800 cST at −5° C. Oils having an EOE content of at least 50% have a viscosity index value of about 208. Viscosity index is an arbitrary number that indicates the resistance of a lubricant to viscosity change with temperature and is readily measured using the American Society for Testing and Materials (ASTM) standard method D2270-91. The viscosity index can be calculated from observed kinematic viscosities of a lubricant at 40° C. and 100° C.; viscosity index values typically range from 0 to greater than 200. Kinematic viscosity values can be determined by Test Methods D 445, IP 71 or ISO 3104. A higher viscosity index value indicates that the viscosity of the oil changes less with a change in temperature. In other words, the higher the viscosity index, the greater the resistance of the lubricant to thicken at low temperatures and thin out at high temperatures. Triacylglycerols typically have higher viscosity index values than those of hydrocarbon oils, i.e. triacylglycerols have a smaller change in viscosity with temperature changes. The viscosity index of oils having an EOE content of at least about 50% is comparable to oils such as HEAR, IMC-6Q canola and TMPTO, and is significantly better than the viscosity index of mineral oils.

Oils having an EOE content of at least about 50% have a lower pour point than other vegetable oils of comparable iodine value (IV). Pour point is the lowest temperature at which the oil flows when chilled, and is typically measured using ASTM standard method D 97. The pour point of oils having an EOE content of at least about 50% can be from about 0° C. to about −30° C.

Surprisingly, oils having an EOE content of at least about 50% are liquid at room temperature and have a melting point of about 6° C. or less. EOE contains the lowest degree of unsaturation possible in a triacylglycerol with unsaturated fatty acids, and has the lowest possible IV (73.3). The fluidity of oils having an EOE content of at least about 50% at room temperature could be due in part to the packing behavior of the TAG, as discussed above. The fatty acid moieties of EOE have varied chain lengths and have double bonds at different positions. In comparison, trierucoyl glycerol (EEE) has three erucic acid moieties esterified to glycerol that contain a double bond at the same position of the fatty acid chain and is solid at room temperature (melting point of about 35° C.).

Oil Compositions

The invention also features oil compositions having high oxidative stability. Such compositions include a vegetable oil and an amount of EOE effective to increase oxidative stability of the vegetable oil. Non-limiting examples of suitable vegetable oils include palm, coconut, corn, soy, sunflower and canola oil. Synthetic EOE or an oil having an EOE content of at least about 50%, based on total triacylglycerol composition, can be added to the vegetable oil. Typically, oxidative stability of the vegetable oil can be increased by addition of about 10% to about 90% of EOE. More preferably, about 40% to about 60% EOE can be added to the vegetable oil. For example, addition of 50% of synthetic EOE to IMC130 oil, a mid-oleic canola oil, can increase the oxidative stability of the vegetable oil from about 38 to about 87 AOM hours.

The invention also features oil compositions that include an oil having an EOE content of at least about 50% based on total triacylglycerol composition and an additive. For example, an oil of the invention can be formulated for industrial applications such as engine lubricants or as hydraulic fluids by addition of one or more additives to an oil having a EOE content of at least about 50% based on total triacylglycerol composition. For example, a transmission fluid for diesel engines can be made that includes antioxidants, anti-foam additives, anti-wear additives, corrosion inhibitors, dispersants, detergents, and acid neutralizers, or combinations thereof. Hydraulic oil compositions can include antioxidants, anti-rust additives, anti-wear additives, pour point depressants, viscosity-index improvers and anti-foam additives or combinations thereof. Specific oil formulations will vary depending on the end use of the oil and can be assessed using standard techniques. Typically, additives are present in amounts totaling from about 0.01% to about 20% based on the weight on the composition.

Typical antioxidants include zinc dithiophosphates, methyl dithiocarbamates, hindered phenols, phenol sulfides, metal phenol sulfides, metal salicylates, aromatic amines, phospho-sulfurized fats and olefins, sulfurized olefins, sulfurized fats and fat derivatives, sulfurized paraffins, sulfurized carboxylic acids, disalieylal-1,2,-propane diamine, 2,4-bis(alkyldithio-1,3,4-thiadiazoles) and dilauryl selenide. TBHQ and Lubrizol product number OS-121056F are particularly useful antioxidants and are typically present in amounts from about 0.01% to about 5%, based on the weight of the composition. In particular, embodiments about 0.01% to about 3.0% of antioxidant is added to an oil of the invention. See U.S. Pat. No. 5,451,334 for additional antioxidants.

Rust inhibitors protect surfaces against rust and include alkylsuccinic type organic acids and derivatives thereof, alkylthioacetic acids and derivatives thereof, organic amines, organic phosphates, polyhydric alcohols and sodium and calcium sulphonates. Anti-wear additives adsorb on metal and provide a film that reduces metal-to-metal contact. In general, anti-wear additives include zinc dialkyldithiophosphates, tricresyl phosphate, didodecyl phosphite, sulfurized sperm oil, sulfurized terpenes and zinc dialkyldithiocarbamate, and are used in amounts from about 0.05% to about 4.5%.

Corrosion inhibitors include dithiophosphates and in particular, zinc dithiophosphates, metal sulfonates, metal phenate sulfides, fatty acids, acid phosphate esters and alkyl succinic acids.

Pour point depressants permit flow of the oil composition below the pour point of the unmodified lubricant. Common pour point depressants include polymethacrylates, wax alkylated naphthalene polymers, wax alkylated phenol polymers and chlorinated polymers are present in amounts of about 1% or less. See, for example, U.S. Pat. Nos. 5,451,334 and 5,413,725. The viscosity index can be increased by adding, for example, polyisobutylenes, polymethacrylates, polyacrylates, ethylene propylene copolymers, styrene isoprene copolymers, styrene butadiene copolymers and styrene maleic ester copolymers.

Anti-foam additives reduce or prevent the formation of a stable surface foam and are typically present in amounts from about 0.00003% to about 0.05%. Polymethylsiloxanes, polymethacrylates, salts of alkylene dithiophosphates, amyl acrylate telomer and poly(2-ethylhexylacrylate-co-ethyl acrylate are non-limiting examples of anti-foam additives.

Detergents and dispersants are polar materials that provide a cleaning function. Detergents include metal sulfonates, metal salicylates and metal thiophosponates. Dispersants include polyamine succinimides, hydroxy benzyl polyamines, polyamine succinamides, polyhydroxy succinic esters and polyamine amide imidazolines.

The invention will be further described in the following examples, which do not limit the scope of the invention described in the claims.

EXAMPLES

Example 1—Synthesis of EOE:

1,3-dihydroxyacetone dimer, 97%, 4-dimethylaminopyridine, 99%, dicyclohexylcarbodiimide, 99%, sodium borohydride, 99% and anhydrous carbon tetrachloride ($CCl_4$), Gold label, were obtained from Aldrich (Milwaukee, Wis.). Erucic acid, 86%, was obtained from Edenor (Hankel Corp., Dusseldorf, Germany) and later purified to 95%. Oleic acid, 97%, was obtained from Sigma Chemical Company (St. Louis, Mo.). Distilled tetrahydrofuran (THF), was obtained from Fisher Scientific (Pittsburgh, Pa).

In the first step, 1,3-dierucoylpropanone was synthesized. Approximately 0.141 moles of 1,3-dihydroxyacetone (12.67 g, 1 equivalent) was added to 300 mls of $CCl_4$ and mixed with 0.282 moles of 4-dimethylaminopyridine (34.35 g, 2 equivalents) and 0.296 moles of erucic acid (100.21 g, 2.1 equivalents). This mixture was gently heated to about 50° C. with stirring until all components were dissolved.

A 1,1' dicyclohexylcarbodiimide (DCC) solution was made by addition of 63.81 g of DCC (0.31 mol, 2.2 equivalents) to 150 mls of $CCl_4$, and added dropwise to the above reaction via an addition funnel over a 30 minute period. The reaction was monitored by IR spectroscopy using a Nicollet FT-IR 5DXC spectrometer with an 60° ATR accessory from Spectra-Tech. Spectra were obtained by adding approximately 1 ml of the reaction mixture to the ATR cell. Typically, about 10 scans were averaged together against a previously obtained background spectrum. The reaction was judged to be complete when no changes were observed in the ester carbonyl region.

Precipitated dicyclohexylurea was removed by vacuum filtration. After evaporation of the $CCl_4$ in a rotovap, a dark brown paste was produced. The paste was dissolved by addition of about 1 liter of hot isopropanol with stirring. Crystals of 1,3 dierucoylpropanone were obtained by leaving the isopropanol overnight at room temperature to crystallize, then filtering and washing with cold (−5° C.) isopropanol. Product was dried in a vacuum oven. The yield ranged from about 35% to about 60%, and was typically about 44% or 43 g.

In the next step, 1,3-dierucoylpropanol was synthesized by dissolving 10 grams of 1,3-dierucoylpropanone in 150 mls of THF and 10 mls of water and chilling to 5° C. After addition of 1 gram of sodium borohydride in small portions, the reaction was monitored by IR spectroscopy as described above. Excess sodium borohydride was destroyed after about 30 minutes by adding acetic acid dropwise until the pH of the mixture was close to 7 as judged by pH paper.

Approximately 300 mls of isopropyl ether was added to the mixture and then washed three times with 50 ml portions of water. The mixture was dried over magnesium sulfate, which was subsequently filtered off. Solvents were evaporated to yield 1,3-dierucoylpropanol. Yield was about 90% to about 95%.

The final product, EOE, was synthesized by the following procedure. A solution of 1,3-dierucoylpropanol was prepared by dissolving 10 g of 1,3-dierucoylpropanol (0.015 mol, 1.1 equivalent) in 150 mls of $CCl_4$. Approximately 0.015 mol of oleic acid (4.24 g, 1.1 equivalent) and 1.65 g of 4-dimethylaminopyridine (0.014 mol, 1 equivalent) were added to the 1,3-dierucoylpropanol solution. A solution of DCC was prepared by addition of 6.16 g of DCC (0.03 mol, 1.2 equivalents) to 15 mls of $CCl_4$ and added dropwise to the reaction mixture over a 10 minute period. The reaction was monitored by IR spectroscopy and was judged complete by the disappearance of the hydroxyl peak. When the reaction was complete, precipitated dicyclohexylcarbourea was filtered off and solvents were evaporated. Column chromatography was used to purify the final product. A glass column (12 in.×2.25 in., Ace Glass) was filled with a slurry of hexane and Davisil 646 silica gel. After approximately 20 grams of product was applied to the silica using an addition funnel attached to the top of the column. Sample was eluted with hexane and dried by rotoevaporation. Yield of the final step was approximately 80%. Overall yield was about 35% to about 40%. It is contemplated that various alternative synthetic and biosynthetic methods could be employed to increase overall yield.

Example 2—Characterization of EOE:

The melting point, onset of crystallization, oxidative stability and viscosity of synthetically prepared EOE was compared to IMC-130, IMC-6Q, soy, 66H and 81S (petroleum based hydrocarbon oils, (National Sun Industries, Cenderlin, N. Dak.) obtained from Lubrizol), TMPTO (Mobil), low erucic acid rapeseed (LEAR), Crambe, IMC/EOE, Soy/EOE, trioleoyl glycerol (Sigma), EEE and HEAR oil. IMC-130, IMC-6Q, soy (refined, bleached and deodorized), LEAR and HEAR oil were obtained from Cargill, Inc. Trioleoyl glycerol (OOO) was produced by esterifying three molecules of erucic acid to one molecule of glycerol in the presence of DMAP and DCC as described above for EOE; OOO is also available commercially from Sigma. The fatty acid compositions of these oils are summarized in Table 1. IMC130/EOE and Soy/EOE are blends of 50% synthetic EOE and 50% vegetable oil.

TABLE 1

| | Fatty Acid Compositions | | | | | | | | |
|---|---|---|---|---|---|---|---|---|---|
| Sample | Palmitate | Stearate | Oleic | Linoleic | α-linolenic | Arachidate | Eicosenoic | Behanate | Erucic |
| IMC-130 | 3.6 | 2.9 | 75 | 11.8 | 3.1 | | | | 0 |
| IMC-6Q | | | 80–87 | 2–5 | 1–4 | | | | 0 |
| SOY | 11 | 4 | 22 | 53 | 7.5 | <1 | <1 | <0.5 | |
| TMPTO | 4 | 1.5 | 73 | 10 | 0.5 | | | | |
| LEAR | 4 | 2 | 56 | 26 | 10 | | 2 | | <2 |
| EOE | | | 33 | | | | | | 66 |
| Crambe | 3.7 | | 20.1 | 11.7 | 5.5 | | 4.6 | 1.6 | 52.8 |

TABLE 1-continued

Fatty Acid Compositions

| Sample | Palmitate | Stearate | Oleic | Linoleic | α-linolenic | Arachidate | Eicosenoic | Behanate | Erucic |
|---|---|---|---|---|---|---|---|---|---|
| IMC-130/EOE | 1.8 | 1.4 | 54 | 5.9 | 1.5 | | | | 33 |
| Soy/EOE | 5.5 | 2 | 27.5 | 26.5 | 3.8 | | | | 33 |
| HEAR | 3 | 1 | 16 | 14 | 10 | 1 | 6 | | 49 |

The onset of crystallization was measured with differential scanning calorimetry (DSC) on a Perkin Elmer Model 7 differential scanning calorimeter. Samples of 7–12 mg were placed in the sample pans, sealed and loaded into the autosampler. The samples were heated from an initial temperature of 30° C. to a final temperature of 75° at a rate of 50° C. per minute and held at this temperature for 10 minutes to allow the material in the pans to melt and become evenly distributed. After cooling the samples to −30° C. at a rate of 5° C. per minute and equilibrating for 15 minutes, a final DSC scan was recorded from −30° C. to 75° C. at a rate of 5° C. per minute.

Viscosity was measured at 40° C. and 100° C. using a Brookfield model DV-II viscometer with a size 18 spindle and standard methodology. A Fisher Scientific circulating water bath model 910 was used to control the temperature of the oils being tested. The viscosity-to-temperature ratio of each oil was characterized by the viscosity index and was calculated using procedure B of ASTM standard method D2270–91.

Oxidative stability was measured using an Oxidative Stability Index instrument, Omnion, Inc., Rockland, Mass. according to AOCS Official Method Cd 12b-92 (revised 1993). This method is an automated replacement for the Active Oxygen Method (AOM) procedure, AOCS Official Method Cd 12-57. AOM hours were determined both in the absence and in the presence of added antioxidants and was calculated using OSI software according to the manufacturer's instructions. Antioxidants used included TBHQ (0.1–1%) and 3% Lubrizol product number OS-121056F.

As shown in Tables 2 and 5, synthetic EOE had a superior combination of high oxidative stability and a high viscosity index value when compared with all other types of tested oils. Synthetic EOE had an oxidative stability of about 84 AOM hours and a viscosity index value of about 208, whereas vegetable oils such as soy and HEAR had viscosity indexes similar to EOE, but had significantly lower oxidative stabilities than EOE. The oxidative stability and viscosity index of IMC-130 oil were both lower than synthetic EOE. Crambe oil had a lower oxidative stability (about 78 AOM hours) and a lower viscosity index (about 187).

Synthetic EOE had a melting point of about 6° C. Blends of vegetable oil and synthetic EOE had melting points that were lower than that of synthetic EOE. For example, a blend of IMC 130 oil and EOE had a melting point of about 3° C. A blend of soy oil and synthetic EOE had a melting point of about −2° C. The onset of crystallization was also decreased to <−30° C. in these blends. In comparison, the onset of crystallization of synthetic EOE was about −19° C.

The oxidative thermal and catalytic stability of synthetic EOE was compared with IMC 130 and OOO (Pfaltz Baver Inc., Waterbury, Conn.) using the Penn State Microoxidation Test. Cvitkovic, E. et al., *ASLE Trans*, 22:395–399 (1979). The microoxidation test was performed with 20 μl samples of unformulated oils at 190° C. with a test duration of 3 hours. The results are shown in Table 3.

The antiwear properties of unformulated samples of synthetic EOE, IMC130 and OOO were evaluated using a mini four-ball wear test performed at 75° C. and 40 kg. The test sequence included 30 minutes using a 10 ml sample of mineral oil followed by 30 minutes using a 6 μl sample of test oil. The results are shown in Table 4.

As shown in Table 5, addition of synthetic EOE to IMC 130 or soy oils increased the oxidative stability of the resulting vegetable oil composition. For example, the oxidative stability of the IMC130/EOE composition was about 87 AOM hours, which was about 38 AOM hours higher than IMC130 oil alone.

The oxidative stability of synthetic EOE can be increased by addition of antioxidants. For example, the oxidative stability of synthetic EOE increased from about 84 AOM hours to about 230 AOM hours by addition of about 3% Lubrizol product number OS-121056F (Table 3). Addition of 0.1% and 1.0% TBHQ increased the oxidative stability of synthetic EOE to about 274 and 563 AOM hours, respectively. In comparison, IMC130 had an oxidative stability of about 182 and 345 AOM hours in the presence of 0.1% and 1.0% TBHQ, respectively.

TABLE 2

Characterization of Oils

| Sample | MP (° C.) | Onset of crystallization (° C.) | VI | Visc 40° | Visc 100° | Density |
|---|---|---|---|---|---|---|
| IMC-130 | −5.82 | <−30 | 188 | 44.4 | 8.95 | 0.9 |
| IMC-6Q | −2.11 | <−30 | 207 | 45.3 | 9.72 | 0.9 |
| SOY | −5 | −14 | 221 | 34.1 | 8.03 | 0.91 |
| 66H | −5.81 | — | 94 | 90.79 | 10.31 | 0.86 |
| 81S | −8 | — | 115 | 51.2 | 7.68 | 0.86 |
| TMPTO | — | — | 211 | 55.3 | 11.61 | 0.9 |
| LEAR | — | — | 224 | 40.7 | 9.36 | 0.91 |
| EOE | 6.2 | −19 | 208 | 59.5 | 12.2 | 0.89 |
| Crambe | 6.85 | −25 | 187 | 63.66 | 11.95 | 0.9 |
| IMC130/EOE | 3.05 | <−30 | 206 | 52.49 | 10.94 | 0.9 |
| Soy/EOE | −2.3 | <−30 | 224 | 37.5 | 8.75 | 0.9 |
| Triolein | 6.22 | <−30 | 181 | 50.54 | 9.72 | 0.91 |
| EEE | 34.9 | 1.32 | | N/A | N/A | |
| HEAR | 2.72 | −30 | 213 | 53.52 | 11.37 | 0.9 |

TABLE 3

Microoxidation

| Sample | % Volatiles | % Deposits |
|---|---|---|
| IMC-130 | 27.4 | 69.8 |
| EOE | 25.1 | 71.8 |
| Trioleoyl glycerol | 25.9 | 75 |

TABLE 4

Mini-Four-Ball Wear Test

| Sample | ΔScar[1], mm | Average f coefficient[2] |
|---|---|---|
| IMC-130 | 0.070 | 0.050 |
| EOE | 0.080 | 0.046 |
| Trioleoyl glycerol | 0.069 | 0.045 |

[1]ΔScar refers to the increase in wear scar diameter (D mm) over the Hertz value or previous D value.
[2]Average f coefficient is the friction coefficient.

TABLE 5

Oxidative Stability in the Presence of Antioxidants

| SAMPLE | Hours AOM Without Antioxidant | Hours AOM With Antioxidant |
|---|---|---|
| IMC-130 | 38.3 | 51.7 |
| IMC-6Q | N/A | N/A |
| SOY | 15.7 | 25.9 |
| 66H | 500+ | 500+ |
| 81S | 500+ | 500+ |
| TMPTO | 0 | 97.28 |
| LEAR | N/A | N/A |
| EOE | 83.7 | 230 |
| Crambe | 77.53 | 226.65 |
| IMC130/EOE | 87 | 90.71 |
| Soy/EOE | 43 | 60 |
| Triolein | 5.67 | 210 |
| EEE | N/A | N/A |
| HEAR | 10.03 | 73.05 |

Example 3—Plants Exhibiting High Levels of Erucic and Oleic Acid:

This examples demonstrates a series of crosses to increase the erucic oil content of Brassica seeds through a reduction in polyunsaturates content and an increase in total monunsaturates content (Table 6). The high erucic acid line used is sold under the trade name Hero (HE101), developed by the University of Manitoba. The Q4275 line has about 82–85% oleic acid and contains a single base transversion from G to A at nucleotide 908 in the fad2-f gene sequence and a G to A transversion at nucleotide 316 in the fad2-d gene sequence. The 663-40 line was produced by a co-suppression event using a transgene containing a napin promotor linked to a fad3 (linoleic desaturase) gene. The 048X058 line contains the 663-40 transgene and a second co-suppression event due to a transgene that includes an oleosin promoter linked to a fad2 (oleic desaturase) gene. Plants were grown in growth chambers under 16 hrs of light at 23/17° C. day/night temperature. Flowers were emasculated prior to opening and covered to prevent cross pollination. On the following day, stigmas of emasculated flowers were pollinated with the desired pollen donor. The F1 seeds were harvested at pod maturity.

TABLE 6

High erucic crossing block

| Cross Number | Female Parent | Female Phenotype | Male Parent | Male Phenotype | Source of Male Phenotype |
|---|---|---|---|---|---|
| 97HEHOA | HE101 | High 22:1 | 048X058 | High 18:1/ Low 18:3 | Transgenes |
| 97HEHOB | HE101 | High 22:1 | Q4275x 663-40 | High 18:1/ Low 18:3 | Mutant/ Transgene |
| 97HEHOC | HE101 | High 22:1 | Q4275x 663-40 | High 18:1/ Low 18:3 | Mutant/ Transgene |

F1 seed generated from the crosses in Table 6 were advanced to the F2 seed generation in the growth chamber. Ten seeds were individually planted for each cross. At flowering the plants were covered with bags to ensure self pollination. The F2 seeds were harvested at maturity.

The seeds were germinated on filter paper at room temperature in the dark. Eighteen to 24 hours after the start of germination, one cotyledon was removed from each seed for extraction of fatty acids. Fatty acid compositions were determined using gas chromatography. Selected F2 half seeds having a high erucic acid content are shown in Tables 7 and 8.

TABLE 7

Half Seed Selection on F2 Seed of 97HEHOA [HE101X(048X052)]

| | Fatty Acid Composition (%) | | | | | | | | | |
|---|---|---|---|---|---|---|---|---|---|---|
| Sample No. | C16:0 | C18:0 | C18:1 | C18:2 | C18:3 | C20:0 | C20:1 | C22:0 | C22:1 | C24:0 | C24:1 |
| VL10186-5 | 2.61 | 1.07 | 29.14 | 5.81 | 2.42 | 0.71 | 14.99 | 0.31 | 40.90 | 0.93 | 0.60 |
| VL10186-33 | 3.47 | 1.32 | 29.73 | 4.38 | 2.98 | 0.86 | 12.22 | 0.44 | 41.21 | 1.50 | 1.28 |
| VL10186-67 | 3.90 | 1.29 | 29.10 | 3.65 | 2.89 | 0.88 | 13.79 | 0.52 | 40.96 | 1.31 | 1.09 |
| VL10186-44 | 2.76 | 1.25 | 34.04 | 2.63 | 1.45 | 0.75 | 16.64 | 0.38 | 38.67 | 0.14 | 0.95 |

TABLE 8

Half Seed Selection on F2 Seed of 97HEHOC [HE101X(Q4275X663-40)]

| Sample No. | Fatty Acid Composition (%) | | | | | | | | | | |
|---|---|---|---|---|---|---|---|---|---|---|---|
| | C16:0 | C18:0 | C18:1 | C18:2 | C18:3 | C20:0 | C20:1 | C22:0 | C22:1 | C24:0 | C24:1 |
| VL10200-214 | 2.24 | 0.74 | 31.66 | 3.01 | 6.24 | 0.46 | 11.79 | 0.41 | 40.60 | 0.86 | 1.57 |
| VL10200-231 | 3.89 | 1.03 | 31.51 | 12.50 | 2.41 | 0.54 | 14.17 | 0.29 | 32.23 | 0 | 0.75 |
| VL10200-238 | 3.36 | 0.95 | 33.19 | 8.99 | 1.66 | 0.55 | 14.35 | 0.21 | 33.61 | 0.83 | 1.02 |
| VL10200-267 | 3.12 | 1.02 | 30.18 | 7.61 | 1.52 | 0.59 | 14.53 | 0.19 | 39.41 | 0.24 | 1.013 |
| VL10203-50 | 2.63 | 0.97 | 31.79 | 8.47 | 1.99 | 0.58 | 14.58 | 0.25 | 37.41 | 0.13 | 0.59 |
| VL10200-293 | 2.71 | 0.78 | 32.83 | 6.85 | 1.88 | 0.46 | 13.11 | 0.32 | 39.18 | 0.82 | 0.67 |

Selected half seeds were planted in soil and grown under growth chamber conditions as described above. At flowering, the plants were covered with bags for self pollination. After maturity, F3 selfed seeds were harvested and analyzed for fatty acid composition. Seeds were analyzed using a sample of 10–15 seeds. F3 lines having high erucic acid content in the endogenous oil are shown are in Tables 9 and 10. An erucic acid content higher than those shown in Tables 9 and 10 can be attained by replacing HE101 in the breeding scheme with a plant line or variety having a higher erucic acid content than HE101, e.g. Mercury, Venus, or Neptune.

TABLE 9

Fatty acid composition of selfed F3 lines of 97HEHOA [HE101X(048X052)]

| Sample No. | Fatty Acid Composition (%) | | | | | | | | | | |
|---|---|---|---|---|---|---|---|---|---|---|---|
| | C16:0 | C18:0 | C18:1 | C18:2 | C18:3 | C20:0 | C20:1 | C22:0 | C22:1 | C24:0 | C24:1 |
| 97HEHO A-74 | 2.51 | 1.03 | 27.44 | 3.72 | 3.55 | 0.65 | 13.60 | 0.30 | 45.57 | 0.14 | 1.03 |
| 97HEHO A-67 | 2.47 | 0.84 | 20.43 | 7.25 | 3.89 | 0.69 | 10.33 | 0.47 | 52.09 | 0.16 | 0.86 |
| 97HEHO A-59 | 2.81 | 1.08 | 27.01 | 7.88 | 2.82 | 0.69 | 16.15 | 0.32 | 39.68 | 0.15 | 0.86 |
| 97HEHO A-33 | 2.53 | 0.79 | 21.90 | 9.52 | 3.55 | 0.53 | 11.51 | 0.31 | 47.59 | 0.13 | 1.08 |
| 97HEHO A-5 | 2.93 | 1.01 | 23.67 | 10.26 | 2.00 | 0.63 | 14.34 | 0.38 | 42.98 | 0.15 | 1.06 |

TABLE 10

Fatty acid composition of selfed F3 lines of 97HEHOC [HE101X(Q4275X663-40)]

| Sample No. | Fatty Acid Composition (%) | | | | | | | | | | |
|---|---|---|---|---|---|---|---|---|---|---|---|
| | C16:0 | C18:0 | C18:1 | C18:2 | C18:3 | C20:0 | C20:1 | C22:0 | C22:1 | C24:0 | C24:1 |
| 97HEHO C-214 | 2.47 | 1.12 | 31.15 | 3.77 | 3.84 | 0.77 | 13.78 | 0.43 | 41.15 | 0.17 | 0.97 |
| 97HEHO C-267 | 2.62 | 1.42 | 31.64 | 6.44 | 1.30 | 0.84 | 15.64 | 0.39 | 38.15 | 0.16 | 0.95 |
| 97HEHO C-293 | 2.73 | 1.13 | 32.08 | 7.23 | 2.18 | 0.72 | 14.88 | 0.41 | 37.17 | 0.17 | 0.81 |
| 97HEHO C-238 | 2.90 | 1.05 | 35.20 | 9.37 | 1.76 | 0.66 | 14.88 | 0.38 | 32.05 | 0.1 | 1.01 |
| 97HEHO C(2)-50 | 2.60 | 0.93 | 31.16 | 5.66 | 2.09 | 0.61 | 14.93 | 0.31 | 40.30 | 0.11 | 0.88 |
| 97HEHO C(2)-156 | 3.19 | 1.71 | 46.56 | 3.05 | 1.59 | 0.94 | 16.41 | 0.40 | 24.67 | 0.19 | 0.83 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A triacylglycerol containing oil having a 1,3-dierucoyl 2-oleoyl glycerol content of at least about 50% based on total triacylglycerol composition.

2. The oil of claim 1, wherein said 1,3-dierucoyl 2-oleoyl glycerol content is from about 60% to about 90%.

3. The oil of claim 2, wherein said 1,3-dierucoyl 2-oleoyl glycerol content is from about 75% to about 90%.

4. The oil of claim 1, said oil having an oxidative stability of from about 80 AOM hours to about 300 AOM hours in the absence of added antioxidants.

5. The oil of claim 4, said oil having an oxidative stability of about 84 AOM hours to about 120 AOM hours.

6. The oil of claim 1, said oil having a viscosity index greater than about 195.

7. An endogenous oil having an erucic acid content of from about 50% to about 70% and an oleic acid content of from about 25% to about 35%, based on total fatty acid composition.

8. The oil of claim 7, wherein about 75% or greater of triacylglycerols of said oil comprise 1,3-dierucoyl 2-oleoyl glycerol.

9. The oil of claim 8, wherein about 75% to about 90% of triacylglycerols of said oil comprise 1,3-dierucoyl 2-oleoyl glycerol.

10. A high oxidative stability composition comprising a vegetable oil and an amount of 1,3-dierucoyl 2-oleoyl glycerol effective to increase oxidative stability of said vegetable oil.

* * * * *